(12) United States Patent
Raines et al.

(10) Patent No.: US 8,950,207 B2
(45) Date of Patent: Feb. 10, 2015

(54) DEVICE FOR STIMULATING ADAPTIVE THERMOGENESIS IN BROWN ADIPOSE TISSUE

(75) Inventors: Mark T. Raines, Austin, TX (US); Dirk H. Buikema, Austin, TX (US)

(73) Assignee: Hyper Wear, Inc., Austin, TX (US)

( * ) Notice: Subject to any disclaimer, the term of this patent is extended or adjusted under 35 U.S.C. 154(b) by 987 days.

(21) Appl. No.: 13/076,325

(22) Filed: Mar. 30, 2011

(65) Prior Publication Data

US 2011/0239682 A1 Oct. 6, 2011

Related U.S. Application Data

(60) Provisional application No. 61/318,990, filed on Mar. 30, 2010.

(51) Int. Cl.
| | |
|---|---|
| *F25D 23/12* | (2006.01) |
| *A61F 7/10* | (2006.01) |
| *A61F 7/00* | (2006.01) |
| *A61F 7/02* | (2006.01) |

(52) U.S. Cl.
CPC ........... *A61F 7/10* (2013.01); *A61F 2007/0009* (2013.01); *A61F 2007/003* (2013.01); *A61F 2007/0292* (2013.01)
USPC ...................................................... 62/259.3

(58) Field of Classification Search
USPC ................................. 62/259.3, 3.5; 2/69, 102
See application file for complete search history.

(56) References Cited

U.S. PATENT DOCUMENTS

| | | | |
|---|---|---|---|
| 3,950,789 A | 4/1976 | Konz et al. | |
| 4,580,408 A | 4/1986 | Stuebner | |
| 4,805,619 A | 2/1989 | Swearingen | |
| 5,038,779 A | 8/1991 | Barry et al. | |
| 5,144,694 A | 9/1992 | Conrad Da oud et al. | |
| 5,146,625 A | 9/1992 | Steele et al. | |
| 5,255,390 A | 10/1993 | Gross et al. | |
| 5,302,806 A | 4/1994 | Simmons et al. | |
| 5,305,471 A | 4/1994 | Steele et al. | |
| 5,692,238 A | 12/1997 | Watson | |
| 5,755,110 A * | 5/1998 | Silvas | 62/259.3 |
| 5,937,441 A | 8/1999 | Raines | |
| 5,970,519 A | 10/1999 | Weber | |
| 6,185,742 B1 * | 2/2001 | Doherty | 2/81 |
| 6,972,029 B2 * | 12/2005 | Mayrhofer et al. | 607/114 |

OTHER PUBLICATIONS

Article entitled "Cold-Activated Brown Adipose Tissue in Healthy Men," by Wouter D. van Marken Lichtenbelt et al. The New England Journal of Medicine, Apr. 9, 2009, pp. 1500-1508.
Article entitled "Cold but not sympathomimetics activates human brown adipose tissue in vivo," by Aaron M. Cypess et al. PNAS vol. 109, No. 25, Jun. 19, 2012, pp. 10001-10005.

\* cited by examiner

*Primary Examiner* — Melvin Jones
(74) *Attorney, Agent, or Firm* — Baker Botts L.L.P.

(57) ABSTRACT

A garment is provided which comprises (a) a first portion constructed from stretchable material that is form fitting to a user's physique and that extends across any of the following body segments of the user; the collar bone, the neck, the upper spine, the armpit area; and (b) a cooling composition disposed in said first portion, said cooling composition comprising a material that may or may not undergo a phase change to apply a cooling effect to the collar bone area of the user.

14 Claims, 12 Drawing Sheets

DEVICE FOR STIMULATING ADAPTIVE THERMOGENESIS IN BROWN ADIPOSE TISSUE

CROSS-REFERENCE TO RELATED APPLICATION

This application claims priority from U.S. Provisional Application No. 61/318,990, which was filed on Mar. 30, 2010, which has the same title, and which is incorporated herein by reference in its entirety.

FIELD OF THE DISCLOSURE

The present disclosure relates generally to devices for exercise, physical therapy or weight loss, and more particularly to a garment adapted to stimulate adaptive thermogenesis in brown adipose tissues.

BACKGROUND OF THE DISCLOSURE

It is often desirable for athletes or individuals undergoing training, physical therapy, or a weight loss regimen to include resistance in an exercise or therapy session. To this end, various devices and types of wearing apparel have been developed over the years that incorporate weight into their designs. By inclusion of weight into the garment itself, the wearer can enjoy the benefits of weight resistance without the inconvenience associated with ankle weights, dumbbells, sandbags and other such separate accessories.

One example of a garment of the foregoing type is disclosed in U.S. Pat. No. 5,144,694 (Daoud et al.), entitled "Exercise Apparel and Weight Packets". The garment disclosed therein includes a vest, pants, spine strap, belt, wrist bands, ankle bands and weight packets. The weight packets include plural rows and plural columns of weight members that are installed in pockets, and the pockets are positioned to distribute the weights about the wearer's body. The placement of the weights is solely maintained by the snugness of the garment's fit to the wearer's body.

Another example of the foregoing type of garment is the exercise vest described in U.S. Pat. No. 5,937,441 (Raines). This weighted exercise and therapeutic vest, when worn by a person involved in either athletic training, physical therapy or a weight reduction program, enhances the benefits of the activity undertaken. The vest has a snug, form-fitting design that clings snugly to the wearer's body, and may be constructed with pockets or other receptacles into which weights may be inserted.

The vest described in Raines represents a notable improvement in the art over previously known exercise vests in that its unique construction provides sufficient support to the applied weights to fix their placement relative to the wearer. This is accomplished through (a) the use of material that resists stretch in one direction while facilitating stretch in another; (b) the inclusion of support straps as an integral component of the vest's construction that join one or more weight compartments in which the weight packets are contained (by continuously connecting the strap to the vest along the entire length of the strap, the load of the weight packet may be distributed across the body of the vest); and (c) the utilization of a rubberized coating applied to at least portions of different components that are positioned into face-to-face engagement during use (the friction experienced between the two rubberized surfaces resists slippage of the weighted portions with respect to the suit and the body of the person wearing it).

DETAILED DESCRIPTION

Figure 1:
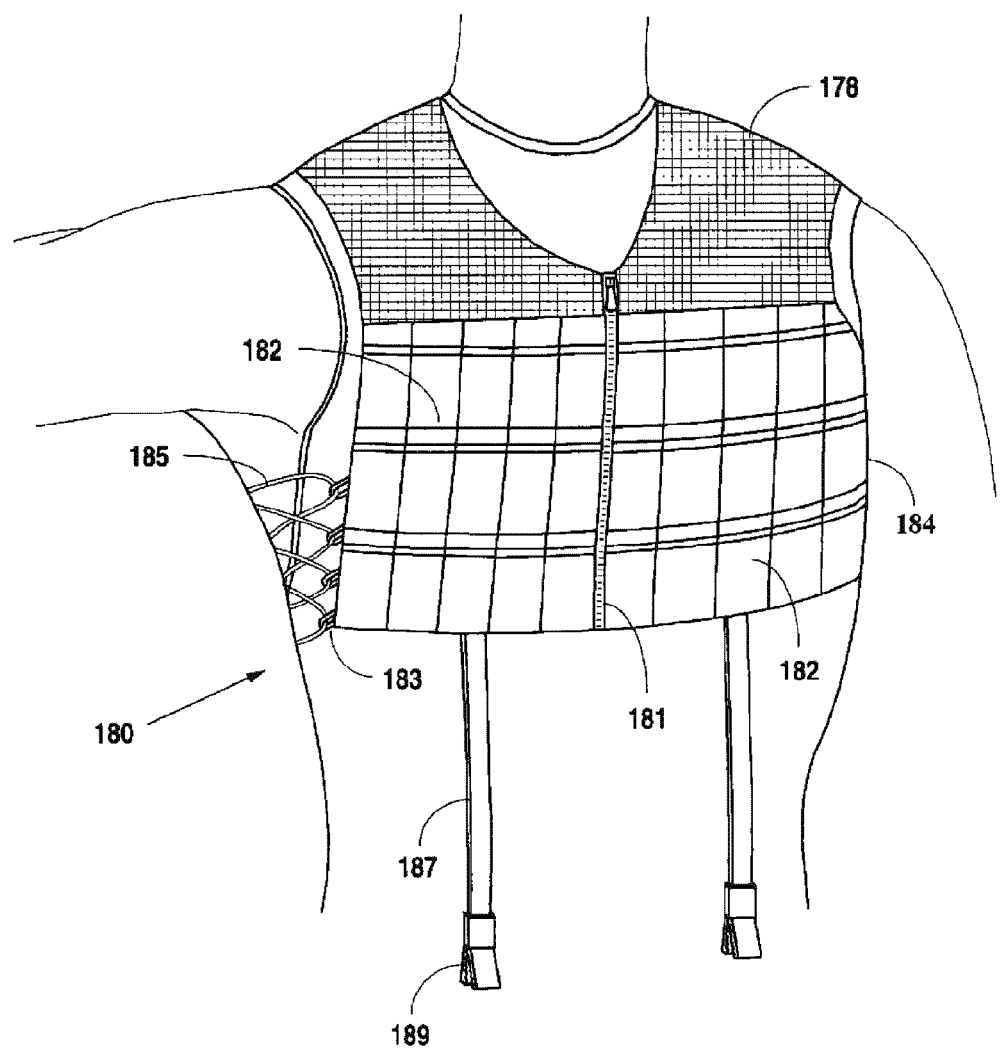
FIG. 1 is an illustration of a first particular, non-limiting embodiment of an exercise or therapeutic garment/device in accordance with the teachings herein.

Although the device of U.S. Pat. No. 5,937,441 (Raines) represents a notable advance in the art, this device was designed primarily as a weight-bearing vest for exercise or therapy, and hence does not address other needs of users. In particular, while such a device may be used to achieve weight loss in the same manner that any other type of exercise device may be utilized for that purpose, it does not, for example, directly enhance the underlying physiological processes that contribute to weight loss and enhance physical fitness. There is thus a need in the art for devices and methodologies which address this infirmity.

It has now been found that the aforementioned needs may be met through the provision of a garment, apparel or other device which permits the thermal stimulation of brown adipose tissues in the body of the user. Such tissues are concentrated, for example, beneath the collar bones, the neck, upper spine, and armpit. Research suggests that it is possible to stimulate adaptive thermogenesis (that is, the generation of energy that the body uses in maintaining a normal body temperature) in such tissues within just 2 hours in a 60° F. room. The devices and methodologies disclosed herein make advantageous use of this discovery by using embedded or incorporated thermo-regulating devices, such as cooling packs, to maintain the brown adipose tissues of a user in a state conducive to adaptive thermogenesis. By way of example, an exercise vest or garment may be made in accordance with the teachings herein which has cooling packs incorporated into a portion thereof that extends over the collar bones, the neck, upper spine, and armpits of the user. The cooling packs may be selected, for example, to maintain a temperature of 58° F. for 3 to 4 hours, and are held snugly in place by the construction of the vest. Various cooling packs offering differing levels of coolness may be selected as thermo-regulating inserts or may be built into the garment.

Studies in animals indicate that brown adipose tissue is important in the regulation of body weight. Indeed, it is possible that individual variations in adaptive thermogenesis can be attributed to variations in the amount or activity of brown adipose tissue. Until recently, the presence of brown adipose tissue was thought to be relevant only in small mammals and infants, and was believed to be of negligible physiologic relevance in adult humans. However, recent research reported in the New England Journal of Medicine (Wouter et al., "Cold Activated Brown Adipose Tissue in Healthy Men, N. Engl. J. Med. 360:15 (Apr. 9, 2009)) suggests that brown adipose tissue may be metabolically important, and the fact that it is reduced yet present in most overweight or obese subjects may make it the target for the treatment of obesity.

The devices and methodologies disclosed herein make advantageous use of the foregoing findings by providing a means to thermally regulate brown adipose tissues in a subject during a workout or therapy session. In particular, the devices and methodologies disclosed herein provide a means by which the brown adipose tissues (as well as surrounding tissues, fluids, or other body masses) in a user may be subjected to a cooling effect which is believed to be advantageous for achieving weight loss through adaptive thermogenesis.

FIG. 1 depicts a first particular, non-limiting embodiment of a thermogenetic garment made in accordance with the teachings herein. The garment 180 depicted therein is an exercise vest which is similar in many respects to the vest disclosed in U.S. Pat. No. 5,937,441 (Raines), which is incorporated herein by reference in its entirety. Thus, the garment 180 comprises an upper portion 178 that extends over the collar bones of the user, and a lower portion 184 that extends across the chest of the user. The material of the upper portion 178 is preferably constructed to permit stretching in lateral or horizontal directions, but to resist vertical stretching. The upper portion 178 has embedded therein one or more cooling packs (which may comprise, for example, one or more materials that undergo a phase change) which are adapted to provide a cooling effect to the collar bone area of the user. Preferably, the cooling packs are adapted to maintain a temperature of 58° F. for 3 to 4 hours. However, it will be appreciated that various materials (including solids, liquids, or gas) may be selected for this purpose that provide a cooling effect which is characterized by different durations and temperatures (or ranges of temperatures). The duration of cooling and the characteristic temperature or temperature range may be chosen based on the desired application.

The garment 180 in this particular embodiment has a lower portion 181 which is optionally equipped with a plurality of cooling pack pockets 182 or other thermo-regulating devices that are arranged generally about a lower portion of the garment 180. The specific configuration of the cooling pack pockets 182 may vary from one embodiment to another. Each of the cooling pack pockets 182 may have a cooling pack inserted therein, with the number of cooling packs and cooling pack pockets 182 utilized being chosen to achieve a desired cooling effect for the vest.

To facilitate use of the vest, a zipper 181 is provided at the front-center of the garment 180. A plurality of loops 183 are also provided at the sides of the garment 180 to further assure that the garment 180 fits snuggly and is variably adjustable. The loops 183 receive a cinch string 185 that may be tightened or loosened to accommodate the particular wearer's body size and to customize the fit of the garment 180.

The garment 180 in this particular embodiment may be further equipped with a set of optional anchor straps 187 to anchor the weighted garment 180 against upward movement with respect to the wearer. Alligator-type clips 189 are provided at terminal lower ends of the anchor straps 187 for releasably fixing the straps 187 to another article of clothing of the wearer. By way of example, these clips 189 may be used to clip the anchor straps 187 to the waistband of a pair of shorts or pants. Of course, it will be appreciated that the garment 180 is not limited to the use of the foregoing clips 189 and straps 187, and that other suitable means may be utilized that achieve a similar end.

Figure 2:
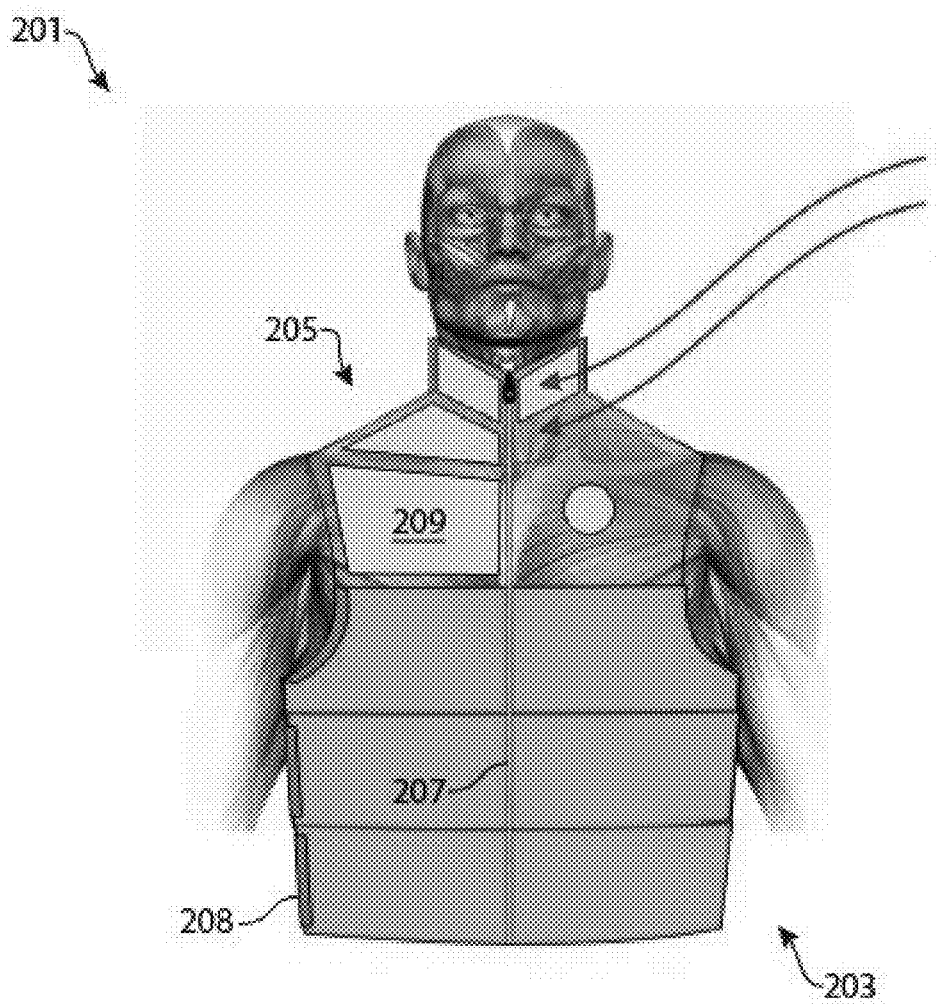
FIGS. 2-3 are illustrations of a second particular, non-limiting embodiment of an exercise or therapeutic garment/device in accordance with the teachings herein.
Figure 3:
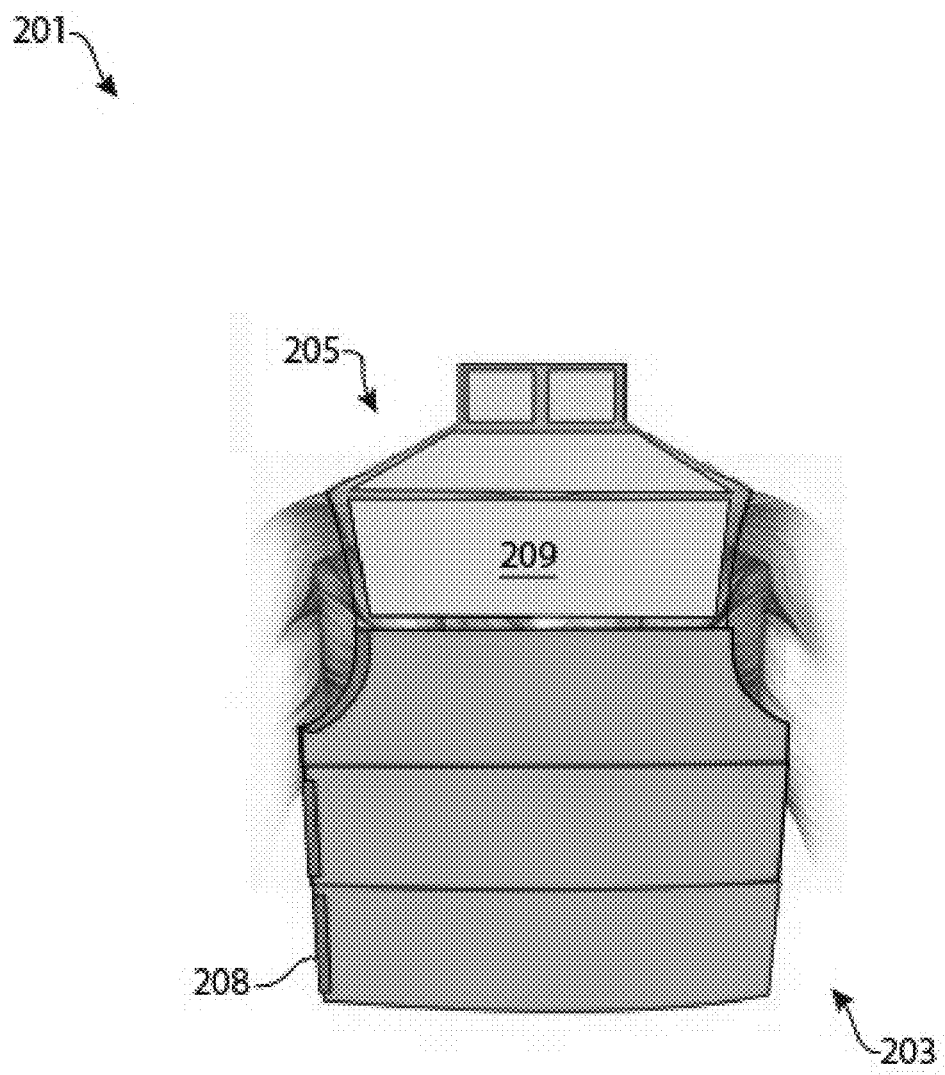

FIGS. 2-3 depict a second particular, non-limiting embodiment of a thermogenetic garment made in accordance with the teachings herein. The garment 201 depicted therein comprises a lower portion 203, an upper portion 205 and a zipper 207 (see FIG. 2) which bisects the garment 201 along a vertical axis. The upper portion 205 is equipped with a plurality of compartments 209, each of which is designed to hold a thermo-regulating device 211 (see FIG. 4). These compartments 209 may be permanently sealed, or may be equipped with a zipper or fastener to allow the thermo-regulating devices 211 to be inserted, removed or replaced. The upper portion 205 of the garment 201 comprises an inner portion 213 which is preferably equipped with a cooling gel layer, and an outer portion 215 which includes the compartments 209.

The lower portion 203 of the garment 201 may have a construction which is the same as, or different from, the upper portion 205. For example, in some embodiments, the lower portion 203 of the garment 201 may also be equipped with a plurality of compartments 209 designed to hold thermo-regulating devices 211. Alternatively, the compartments 209 in the lower portion 203 may be used to hold weights or a material, such as sand or metal particles, which add weight or resistance to the garment 201.

Various materials may be used in the construction of the garment 201. Preferably, the garment is equipped with a base material comprising a one-way stretch fabric, such as the fabrics based on polyurethane-polyurea copolymers sold under the trade names LYCRA® and SPANDEX®. The garment is also preferably equipped with a top or outer material which preferably comprises one or more synthetic rubbers. Suitable materials of this type include the fabrics based on polychloroprene which are sold under the trade name NEOPRENE®.

Figure 4:
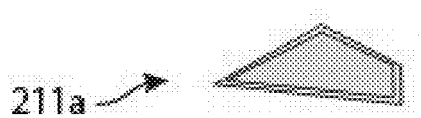
FIG. 4 is an illustration of some particular, non-limiting embodiments of cooling packs which may be utilized in the garments and devices described herein.
Figure 4:
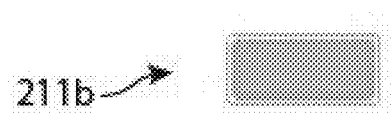
Figure 4:
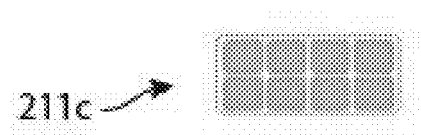
Figure 5:
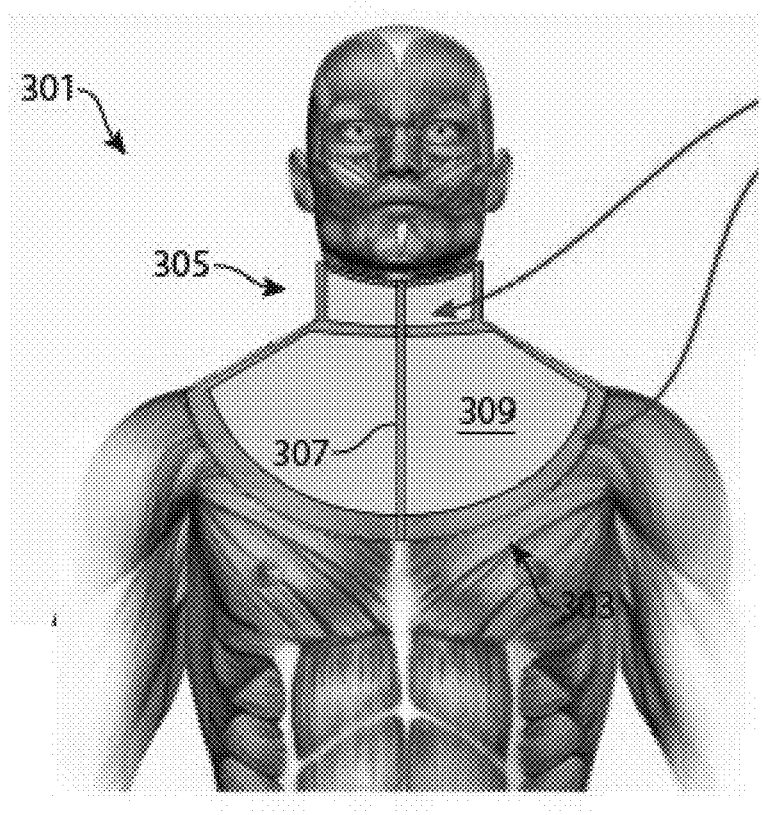
FIGS. 5-8 are illustrations of a third particular, non-limiting embodiment of an exercise or therapeutic garment/device in accordance with the teachings herein.
Figure 6:
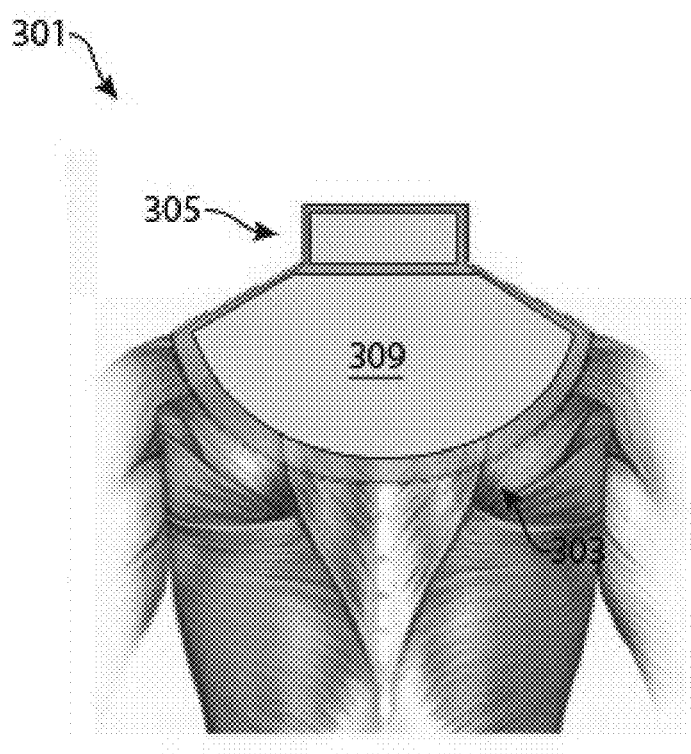

FIG. 4 illustrates some particular, non-limiting examples of thermo-regulating devices 211 which may be utilized in the garment of FIGS. 2-3. These devices, which may be the same as or different from the cooling packs described with respect to the embodiment of FIG. 1, are designed to fit inside of suitably sized pockets provided in the upper portion 205 of the garment 201, and are preferably designed to lay flat against the body of the user. The thermo-regulating devices may be custom shaped (see 211a), and may have a single compartment (see 211b) or multi-compartment (see 211c) structure. Moreover, while the thermo-regulating devices are preferably adapted to provide a cooling effect, embodiments are also possible in which these devices provide a heating effect.

FIGS. 5-8 illustrate another particular, non-limiting embodiment of a thermogenetic garment made in accordance with the teachings herein. The garment 301 depicted therein comprises a lower portion 303 that extends over the neck and shoulder blades of the user, and an upper portion 305 that extends around the neck of the user. A seam 307 equipped with a hook and loop type faster, zipper, or other suitable releasable fastener is provided to allow the garment 301 to be readily positioned on, or removed from, the body of the user.

Figure 7:
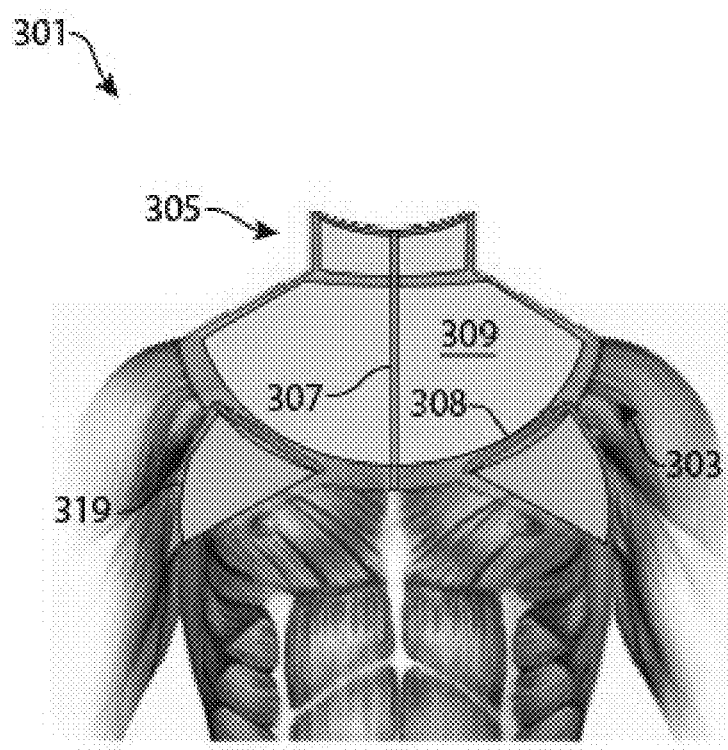
Figure 8:
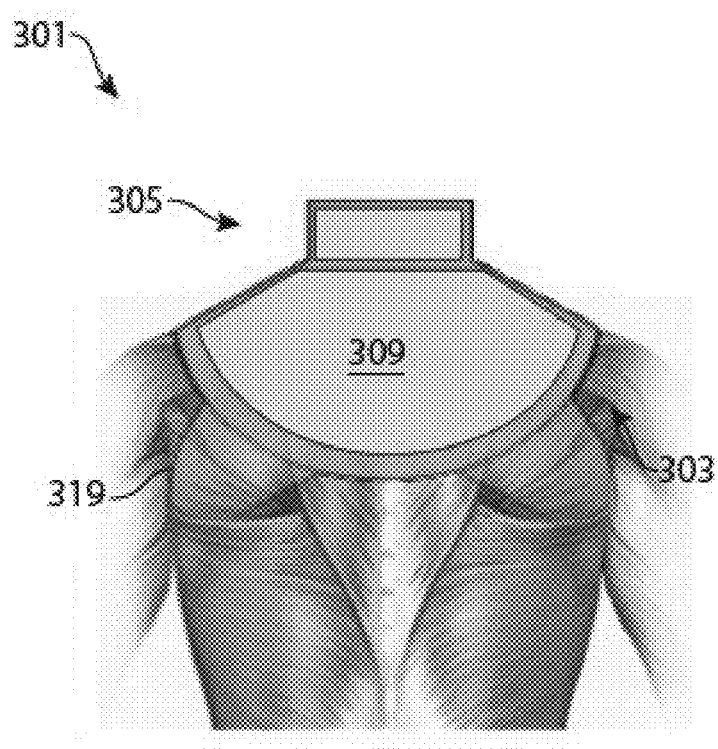
Figure 9:
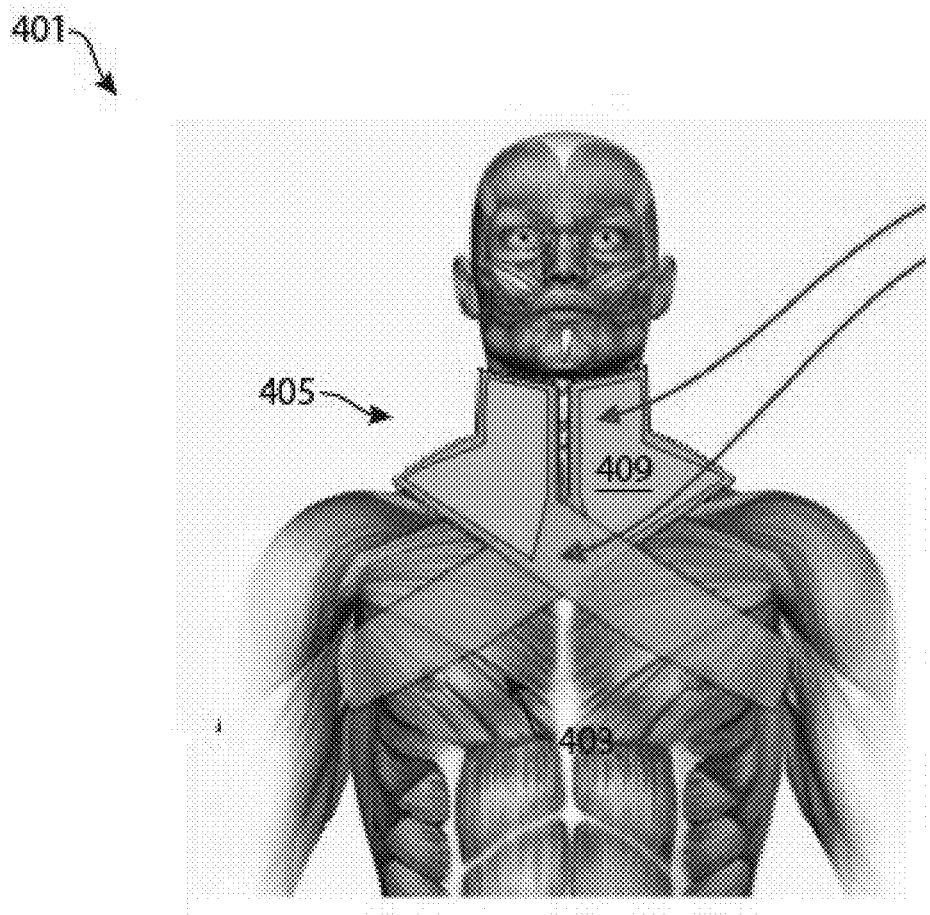
FIGS. 9-12 are illustrations of a fourth particular, non-limiting embodiment of an exercise or therapeutic garment/device in accordance with the teachings herein.

As shown in FIGS. 7-8, in some variations of this embodiment, an auxiliary portion 319 is provided which extends across the armpits of the user. Preferably, the auxiliary portion 319 is releasably attached to the garment 301 by way of a hook-and-loop type fastener 308, although it will be appreciated that a zipper or other suitable means as are known to the art may be utilized to releasably attach the auxiliary portion 319 to the lower portion 303 of the garment 301. However, embodiments are also contemplated where the auxiliary portion 319 is permanently attached to the garment 301.

The garment 301 may have the same general construction as the garment 201 depicted in FIGS. 2-3. Like that garment 201, the garment 301 is equipped with one or more compartments 309 which contain a thermo-regulating devices.

Figure 10:
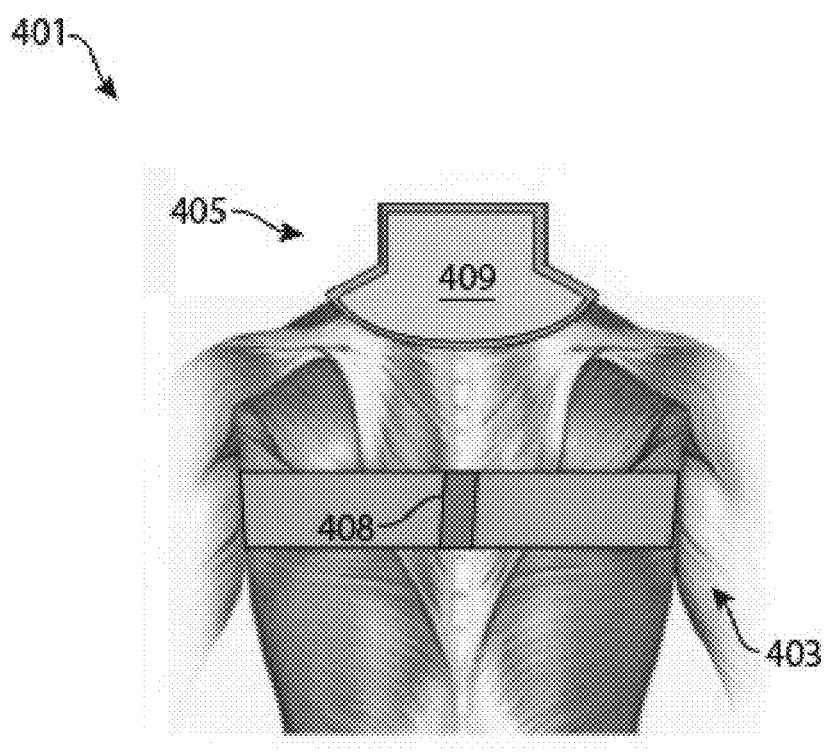
Figure 11:
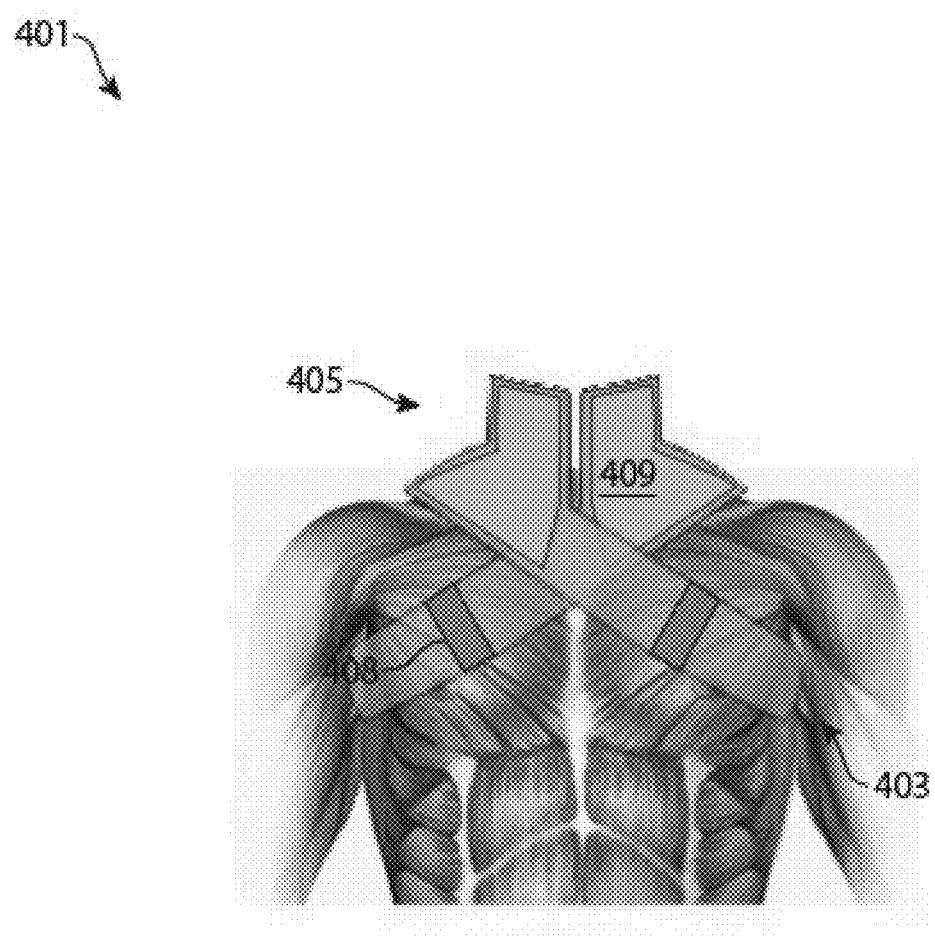
Figure 12:
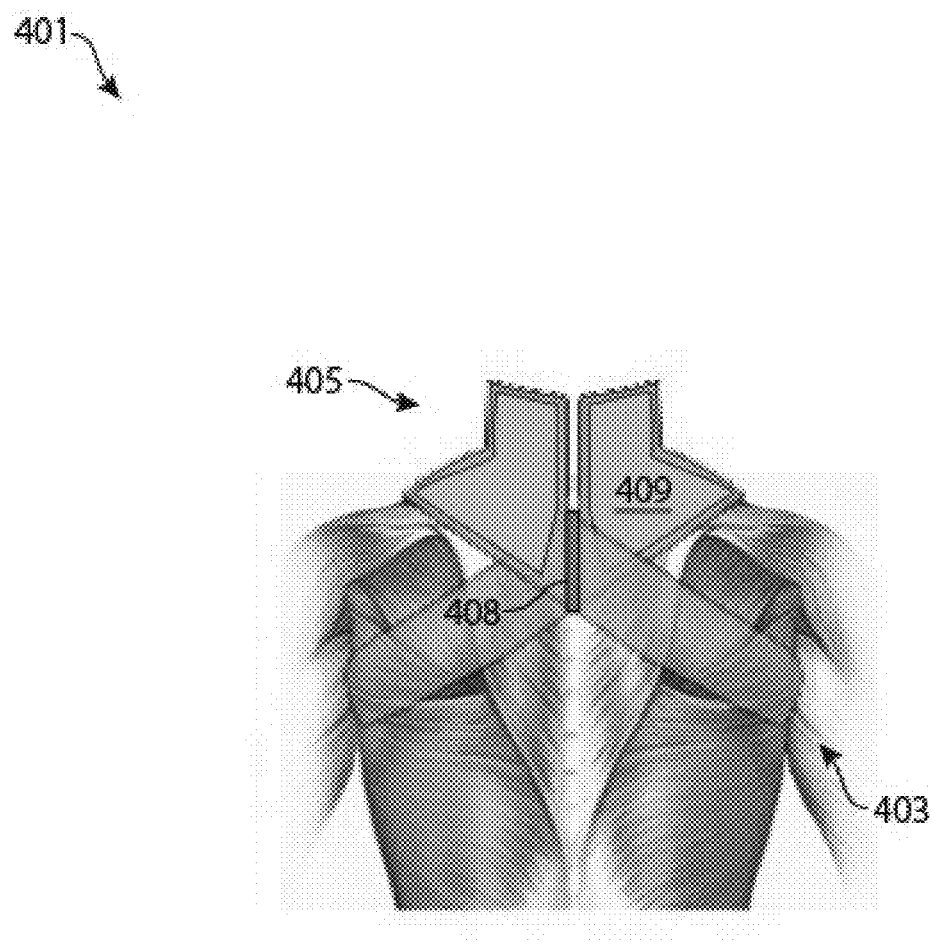

FIGS. 9-12 illustrate a further particular, non-limiting embodiment of a thermogenetic garment made in accordance with the teachings herein. The garment 401 depicted therein comprises a lower portion 403 that extends across the shoulder blades and spine of the user, and an upper portion 405 that extends around the neck of the user. As seen in FIG. 10, a seam 408 equipped with a hook and loop type faster, zipper, or other suitable releasable fastener is provided to allow the garment 401 to be readily positioned on, or removed from, the body of the user. FIGS. 11 and 12 show alternate variations of this embodiment in which the seam 408 is positioned in different areas of the garment 401.

While the foregoing description has focused primarily on the adaptation of a garment to stimulate adaptive thermogenesis by applying a cooling effect to brown adipose tissues occurring in the collar bone area, the neck, the upper spine, and the armpit of the user, one skilled in the art will appreciate that, more generally, garments may be made in accordance with the teachings herein which are adapted to apply a cooling effect to brown adipose tissues wherever they may occur in the body of the user. In some such embodiments, the cooling effect may be localized to the brown adipose tissues, though embodiments are also possible in accordance with the teachings herein which apply such an effect to a larger area, or even to the entire body of the user.

The above description of the present invention is illustrative, and is not intended to be limiting. It will thus be appreciated that various additions, substitutions and modifications may be made to the above described embodiments without departing from the scope of the present invention. Accordingly, the scope of the present invention should be construed in reference to the appended claims.

What is claimed is:

1. A garment, comprising:
a first portion constructed from stretchable material that is form fitting to a user's physique and that extends across a collar bone area of the user; and
a cooling composition disposed in said first portion, said cooling composition comprising a material that undergoes a phase change to apply a cooling effect to the collar bone area of the user and maintains a temperature of 58° F. for at least three hours.

2. The garment of claim 1, further comprising a second portion that is form fitting to the user's torso.

3. The garment of claim 2, wherein said second portion is releasably attached to said first portion.

4. The garment of claim 1, wherein said composition is disposed in a single or plurality of phase change packs.

5. The exercise garment of claim 1, wherein said cooling composition maintains a temperature of 58° F. for at least four hours.

6. A garment comprising:
a first portion constructed from stretchable material that is form fitting to a user's physique and that extends across a collar bone area of the user;
a cooling composition disposed in said first portion, said cooling composition comprising a material that undergoes a phase change to apply a cooling effect to the collar bone area of the user;
a second portion that is form fitting to the user's torso;
a cooling packet attachable to said second portion for relatively fixed location upon the user's physique; and
at least one support strap for distributing the load of said cooling packet about the surface area of the second portion.

7. The garment of claim 6, wherein said second portion comprises a material which is stretchable in a first direction and which resists stretching in a second direction.

8. The garment of claim 7, wherein said second direction is substantially perpendicular to said first direction.

9. The garment of claim 7, wherein said first direction is substantially horizontal with respect to an erect user in an arms to the side position, and wherein said second direction is substantially vertical with respect to an erect user in an arms to the side position.

10. The garment of claim 9, wherein said support strap is constructed integrally with said second portion for supporting said weight packet in the second direction.

11. The garment of claim 7, further comprising:
at least one weight compartment constructed integrally with said second portion for receiving said cooling packet, wherein said cooling packet is confined within said cooling compartment so that said cooling packet fits snugly to the user's physique and minimally extends therefrom, and wherein said support strap is constructed integrally with said weight compartment.

12. The garment of claim 7, further comprising:
an outer shell covering portions of said first portion and said cooling packet for securely fixing said cooling packet's position upon the user; and
a plurality of cooling compartments positioned upon said first portion so that a plurality of cooling packets may be selectively distributed about the user.

13. The garment of claim 12, wherein said stretchable material from which said second portion is constructed is breathable spandex or elastic weave that allows perspiration of the user to pass therethrough thereby providing comfort to the user, wherein said cooling packets are elastic pouches with insertable cooling packs, and further comprising an adjustable securing band integrally constructed into select cooling compartments that are positioned upon said appendage segment for constriction about said select cooling compartments.

14. The garment of claim 6, wherein the support strap comprises supporting internal stitching or weaving.

* * * * *